(12) United States Patent
Solem et al.

(10) Patent No.: US 6,997,951 B2
(45) Date of Patent: *Feb. 14, 2006

(54) METHOD AND DEVICE FOR TREATMENT OF MITRAL INSUFFICIENCY

(75) Inventors: Jan Otto Solem, Stetten (CH); Per-Ola Kimblad, Lund (SE); Randolf von Oepen, Tubingen (DE); Bodo Quint, Rottenburg-Seebronn (DE); Gerd Seibold, Ammerbuch (DE); Kenneth J. Michlitsch, Livermore, CA (US); Suk-Woo Ha, Langwiesen (CH); Karl-Ludwig Eckert, Marthalen (CH); Ib Joergensen, Haigerloch (DE); Stevan Nielsen, Rottenberg (DE)

(73) Assignee: Edwards Lifesciences AG, (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/329,720

(22) Filed: Dec. 24, 2002

(65) Prior Publication Data

US 2004/0039443 A1    Feb. 26, 2004

Related U.S. Application Data

(63) Continuation-in-part of application No. 09/775,677, filed on Feb. 5, 2001, which is a continuation-in-part of application No. 09/345,475, filed on Jun. 30, 1999, now Pat. No. 6,210,432.

(60) Provisional application No. 60/344,121, filed on Dec. 28, 2001.

(51) Int. Cl.
*A61F 2/24* (2006.01)

(52) U.S. Cl. ............... 623/2.37; 623/2.36; 623/1.1; 600/16

(58) Field of Classification Search ............ 623/11.11, 623/23.7, 1.1, 1.11, 1.15, 1.16, 1.2, 1.23, 623/1.3, 1.31, 2.36, 2.37, 1.22, 1.18; 600/16–18; 606/108, 191–198; 128/898
See application file for complete search history.

(56) References Cited

U.S. PATENT DOCUMENTS

| | | | |
|---|---|---|---|
| 4,164,046 A | 8/1979 | Cooley | |
| 4,655,771 A | 4/1987 | Wallsten | |
| 4,954,126 A | 9/1990 | Wallsten | |
| 5,006,106 A | 4/1991 | Angelchik | |

(Continued)

FOREIGN PATENT DOCUMENTS

DE     196 05 042 A1    1/1998

(Continued)

OTHER PUBLICATIONS

Laaksovirta et al., *Expansion and bioabsorption of the self-reinforced lactic and glycolic acid copolymer prostatic spiral stent*, PubMed, Excerpt from J Urol Sep. 2001; 166(3):919-22, one sheet.

(Continued)

*Primary Examiner*—David J. Isabella
*Assistant Examiner*—Urmi Chattopadhyay
(74) *Attorney, Agent, or Firm*—David L. Hauser

(57) ABSTRACT

A device for treatment of mitral annulus dilation is disclosed, wherein the device comprises two states. In a first of these states the device is insertable into the coronary sinus and has a shape of the coronary sinus. When positioned in the coronary sinus, the device is transferable to the second state assuming a reduced radius of curvature, whereby the radius of curvature of the coronary sinus and the radius of curvature as well as the circumference of the mitral annulus is reduced.

7 Claims, 15 Drawing Sheets

U.S. PATENT DOCUMENTS

| | | |
|---|---|---|
| 5,061,275 A | 10/1991 | Wallsten et al. |
| 5,064,435 A | 11/1991 | Porter |
| 5,104,404 A | 4/1992 | Wolff |
| 5,163,955 A | 11/1992 | Love et al. |
| 5,170,802 A | 12/1992 | Mehra |
| 5,383,892 A * | 1/1995 | Cardon et al. ............. 623/1.16 |
| 5,476,471 A | 12/1995 | Shifrin et al. |
| 5,534,007 A | 7/1996 | St. Germain et al. |
| 5,571,135 A | 11/1996 | Fraser et al. |
| 5,584,879 A | 12/1996 | Reimold et al. |
| 5,593,442 A | 1/1997 | Klein |
| 5,607,444 A * | 3/1997 | Lam .......................... 606/194 |
| 5,674,280 A | 10/1997 | Davidson et al. |
| 5,713,949 A | 2/1998 | Jayaraman |
| 5,741,274 A | 4/1998 | Lenker et al. |
| 5,817,126 A * | 10/1998 | Imran ........................ 623/1.15 |
| 5,824,071 A | 10/1998 | Nelson et al. |
| 5,876,419 A | 3/1999 | Carpenter et al. |
| 5,911,732 A | 6/1999 | Hojeibane |
| 5,919,233 A | 7/1999 | Knopf et al. |
| 5,980,552 A | 11/1999 | Pinchasik et al. |
| 6,027,525 A | 2/2000 | Suh et al. |
| 6,071,292 A | 6/2000 | Makower et al. |
| 6,093,203 A * | 7/2000 | Uflacker ..................... 623/1.12 |
| 6,183,411 B1 | 2/2001 | Mortier et al. |
| 6,203,556 B1 | 3/2001 | Evans et al. |
| 6,210,432 B1 | 4/2001 | Solem et al. |
| 6,221,103 B1 | 4/2001 | Melvin |
| 6,248,119 B1 | 6/2001 | Solem |
| 6,250,308 B1 | 6/2001 | Cox |
| 6,264,602 B1 | 7/2001 | Mortier et al. |
| 6,264,691 B1 | 7/2001 | Gabbay |
| 6,325,826 B1 * | 12/2001 | Vardi et al. ................. 623/1.35 |
| 6,343,605 B1 | 2/2002 | Lafontaine |
| 6,350,277 B1 | 2/2002 | Kocur |
| 6,402,679 B1 | 6/2002 | Mortier et al. |
| 6,402,680 B1 | 6/2002 | Mortier et al. |
| 6,402,781 B1 | 6/2002 | Langberg et al. |
| 6,409,760 B1 | 6/2002 | Melvin |
| 6,537,314 B1 | 3/2003 | Langberg et al. |
| 6,569,198 B1 | 5/2003 | Wilson et al. |
| 6,626,899 B1 | 9/2003 | Houser et al. |
| 6,656,221 B1 | 12/2003 | Taylor et al. |
| 6,669,687 B1 | 12/2003 | Saadat |
| 6,676,702 B1 | 1/2004 | Mathis |
| 6,702,826 B1 | 3/2004 | Liddicoat et al. |
| 6,706,065 B1 | 3/2004 | Langberg et al. |
| 6,709,456 B1 | 3/2004 | Langberg et al. |
| 6,764,510 B1 | 7/2004 | Vidlund et al. |
| 6,790,231 B1 | 9/2004 | Liddicoat et al. |
| 6,797,001 B1 | 9/2004 | Mathis et al. |
| 6,800,090 B1 | 10/2004 | Alferness et al. |
| 6,810,882 B1 | 11/2004 | Langberg et al. |
| 6,824,562 B1 | 11/2004 | Mathis et al. |
| 6,890,353 B1 * | 5/2005 | Cohn et al. ................. 623/2.37 |
| 2001/0018611 A1 | 8/2001 | Solem et al. |
| 2001/0044568 A1 | 11/2001 | Langberg et al. |
| 2002/0016628 A1 | 2/2002 | Langberg et al. |
| 2002/0019660 A1 | 2/2002 | Gianotti et al. |
| 2002/0022880 A1 | 2/2002 | Melvin |
| 2002/0042621 A1 | 4/2002 | Liddicoat et al. |
| 2002/0087173 A1 | 7/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0124857 A1 | 9/2002 | Schroeppel |
| 2002/0151961 A1 | 10/2002 | Lashinski et al. |
| 2002/0169502 A1 | 11/2002 | Mathis |
| 2002/0169504 A1 | 11/2002 | Alferness et al. |
| 2002/0183835 A1 | 12/2002 | Taylor at el. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0105520 A1 | 6/2003 | Alferness et al. |
| 2003/0130730 A1 | 7/2003 | Cohn et al. |
| 2003/0135267 A1 | 7/2003 | Solem et al. |
| 2003/0144697 A1 | 7/2003 | Mathis et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102841 A1 | 5/2004 | Langberg et al. |
| 2004/0133192 A1 | 7/2004 | Houser et al. |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0267358 A1 | 12/2004 | Reitan |

FOREIGN PATENT DOCUMENTS

| | | |
|---|---|---|
| DE | 196 11 755 A1 | 2/1998 |
| EP | 0 727 239 A2 | 8/1996 |
| WO | WO 95/16407 | 6/1995 |
| WO | WO 96/40356 | 12/1996 |
| WO | WO 98/18411 | 5/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 2004/084746 A2 | 10/2004 |

OTHER PUBLICATIONS

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in denistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1998; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp. 5, ISSN 0009-2347, Mairin Brennan, three sheets.

Stikeman, *Total Recall*, Technology Review—Innovation: Total Recall, An MIT Enterprise Technology Review, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP01/10371, 4 sheets.

International Search Report dated Mar. 15, 2000 for National application No. 9902455-6, 3 sheets.

International Search Report dated Oct. 9, 2002 for National application No. 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 183-93, one sheet.

* cited by examiner

METHOD AND DEVICE FOR TREATMENT OF MITRAL INSUFFICIENCY

REFERENCE TO RELATED APPLICATIONS

The present application is a continuation-in-part of U.S. patent application Ser. No. 09/775,677, filed Feb. 5, 2001, which is a continuation-in-part of U.S. patent application Ser. No. 09/345,475, filed Jun. 30, 1999, now U.S. Pat. No. 6,210,432. The present application also claims priority of provisional application No. 60/344,121 entitled METHOD AND DEVICE FOR TREATMENT OF MITRAL INSUFFICIENCY, filed Dec. 28, 2001.

FIELD OF THE INVENTION

The present invention relates to a device for treatment of mitral insufficiency and, more specifically, for treatment of dilation of the mitral annulus.

BACKGROUND OF THE INVENTION

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilation is a major component in the pathology of mitral insufficiency regardless of cause. Moreover, many patients have a mitral insufficiency primarily or exclusively due to posterior annular dilation, since the annulus of the anterior leaflet does not dilate because it is anchored to the fibrous skeleton of the base of the heart.

Studies of the natural history of mitral insufficiency have found that totally asymptomatic patients with severe mitral insufficiency usually progress to severe disability within five years. Currently, the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair theoretically is possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but non-elastic, like the Duran ring or the Cosgrove-Edwards ring.

Effective treatment of mitral insufficiency currently requires open-heart surgery, by the use of total cardiopulmonary bypass, aortic cross-clamping and cardioplegic cardiac arrest. To certain groups of patients, this is particularly hazardous. Elderly patients, patients with a poor left ventricular function, renal disease, severe calcification of the aorta, and those having previous cardiac surgery or other concomitant diseases would in particular most likely benefit from a less invasive approach, even if repair is not complete.

In view of these drawbacks of previously known treatments, it would be desirable to provide a minimally invasive approach to treat mitral insufficiency, i.e., without the need for cardiopulmonary bypass and without opening of the chest and heart.

It also would be desirable to provide a reduction of the mitral annulus using only catheter based technology.

It further would be desirable to provide a treatment for mitral insufficiency that minimizes trauma to a patient's vasculature while using catheter based technology.

SUMMARY OF THE INVENTION

In view of the foregoing, it is an object of the present invention to provide a minimally invasive approach to treat mitral insufficiency, i.e., without the need for cardiopulmonary bypass and without opening of the chest and heart.

It is also an object of the present invention to provide a reduction of the mitral annulus using only catheter-based technology.

It is another object of the present invention to provide a treatment for mitral insufficiency that minimizes trauma to a patient's vasculature while using catheter based technology.

These and other objects of the present invention are achieved by providing a device for treatment of mitral insufficiency, whereby the circumference of the mitral valve annulus is reduced when the device is deployed and/or actuated in at least a portion of the coronary sinus.

The device in accordance with principles of the present invention may comprise one or more components suitable for deployment in the coronary sinus and adjoining coronary veins. The device may be configured to bend in-situ to apply a compressive load to the mitral valve annulus with or without a length change, or may include multiple components that are drawn or contracted towards one another to reduce the circumference of the mitral valve annulus. Any of a number of types of anchors may be used to engage the surrounding vein and tissue, including hooks, barbs, flanges, partial or completely through-wall tee structures, or biological anchoring. Where multiple components are provided, reduction of the mitral valve annulus may be accomplished during initial deployment of the device, or by biological actuation during subsequent in-dwelling of the device.

In one embodiment comprising multiple components, the device comprises proximal and distal stent sections, wherein the proximal stent section comprises a deployable flange. The stent sections are delivered into the coronary sinus in a contracted state, and then are deployed within the coronary venous vasculature so that the flange engages the coronary sinus ostium. A cinch mechanism, comprising, for example, a plurality of wires and eyelets, is provided to reduce the distance between proximal and distal stent sections, thereby reducing the circumference of the mitral valve annulus.

In an alternative embodiment, the distal stent is replaced by or includes a suitably-shaped distal anchor that is disposed within or through the left ventricular myocardium. The distal anchor may be in the form of a Tee-shape or barbed section, and engages the ventricular myocardium, or extends into the left ventricle, to provide a distal fixation point. As in the preceding embodiment, a cinch mechanism is provided to shorten a structure, such as a wire, that extends between the proximal stent and the distal anchor.

The distal anchor may be used alone or in conjunction with the proximal flange of the preceding embodiment.

In a further alternative embodiment, a balloon catheter is used wherein a balloon in fluid communication with a lumen of the catheter comprises a predetermined deployed shape. A stent, which may be compressed onto the balloon in a contracted state, then is plastically deformed by the balloon within the coronary sinus, and the stent substantially conforms to the predetermined shape of the balloon in a deployed state. The balloon preferably comprises a convex shape, so that the stent will assume the convex shape of the balloon and bend the coronary sinus accordingly. The shape of the stent, convex or otherwise, will be configured to reduce the circumference of the mitral valve annulus when deployed in the coronary sinus.

The configuration of cells of the stent also may be varied to encourage the stent to assume a convex shape upon deployment. For example, one side of the stent may be configured to expand a greater amount than the other side, thereby imparting a convex curvature upon the stent. To facilitate proper positioning of the stent within the coronary sinus, an intravascular ultrasound transducer or radiopaque marker bands may be used to align the correct side of the stent adjacent the mitral valve annulus.

In a yet further embodiment, the proximal and distal stent sections are directly coupled to one another by a central section, so that expansion of the central section causes the proximal and distal stent sections to be drawn together. In this embodiment, however, the central section includes one or more biodegradable structures, such as biodegradable sutures, that retain the central section in its contracted state until the vessel endothelium has overgrown a portion of the proximal and distal stent sections, thereby providing biological anchoring of the proximal and distal stent sections. After the proximal and distal stent sections have become endothelialized, the biodegradable structure degrades, releasing the central section and enabling it to expand. The central section thereby applies a tensile load to the proximal and distal stent sections, causing a reduction in the circumference of the mitral valve annulus.

A yet further alternative embodiment comprises a series of linked segments that are capable of relative rotational and telescoping movement. In a preferred embodiment, each segment includes a ball element that couples to a socket element on an adjacent segment. The ball and socket connections permit the segments of the device to become angled relative to one another so that the device is capable of assuming a three-dimensional curvature. A cinch wire extends through a passage in the segments and permits the device to be cinched rigidly into a predetermined shape. Some segments also may include telescoping joints that permit the overall length of the device to be reduced upon actuation of the cinch wire. The cinch wire may include either a locking mechanism attached to the cinch wire or alternatively may include striations on the contacting ball and socket surfaces that permit the segments to rigidly engage one another when cinched.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention takes advantage of the position of the coronary sinus being close to the mitral annulus. This makes repair possible by the use of current catheter-guided techniques by deploying one element in the coronary venous vasculature that applies a load to, and reshapes, the adjacent posterior portion of the mitral annulus.

The coronary veins drain blood from the myocardium to the right atrium. The smaller veins drain blood directly into the atrial cavity, and the larger veins accompany the major arteries and run into the coronary sinus which substantially encircles the mitral orifice and annulus. The coronary sinus runs in the posterior atrioventricular groove, lying in the fatty tissue between the left atrial wall and the ventricular myocardium, before draining into the right atrium between the atrial septum and the post-Eustachian sinus.

Figure 1:
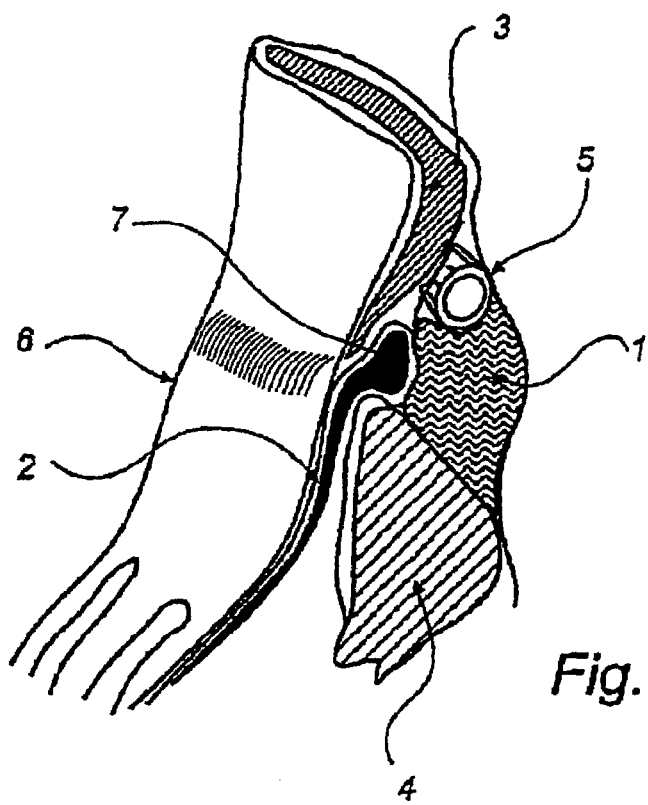
FIG. 1 is a cross-sectional view of a part of a heart.

FIG. 1 is a cross-sectional view through the heart area of posterior atrioventricular groove 1, which is filled with fatty tissue. It shows posterior leaflet 2 of the mitral valve and adjoining parts 3, 4 of the atrial myocardium and the ventricular myocardium. Coronary sinus 5 is shown close to mitral annulus 6 and behind attachment 7 of posterior leaflet 2. Since coronary sinus 5 substantially encircles mitral annulus 6, a reduction of the radius of curvature of bent coronary sinus 5 also will result in a diameter and circumference reduction of mitral annulus 6.

In an adult, the course of coronary sinus 5 may approach within 5–15 mm of the medial attachment of posterior leaflet 2 of the mitral valve. Preliminary measurements performed at autopsies of adults of normal weight show similar results, with a distance of 5.3±0.6 mm at the medial attachment and about 10 mm at the lateral aspect of posterior leaflet 2. The circumference of coronary sinus 5 was 18.3±2.9 mm at its ostium (giving a sinus diameter of the septal aspect of the posterior leaflet of 5.8±0.9 mm) and 9.7±0.6 mm along the lateral aspect of posterior leaflet 2 (corresponding to a sinus diameter of 3.1±0.2 mm).

In accordance with the principles of the present invention, devices and methods for treating mitral insufficiency are provided, wherein the circumference of the mitral valve annulus is reduced when the device is deployed and/or actuated in at least a portion of the coronary sinus.

Devices constructed in accordance with principles of the present invention may comprise one or more components suitable for deployment in the coronary sinus and adjoining coronary veins. The device may be configured to bend in-situ to apply a compressive load to the mitral valve annulus with or without a length change, or may include multiple components that are drawn or contracted towards one another to reduce the circumference of the mitral valve annulus. Any of a number of types of anchors may be used to engage the surrounding vein and tissue, including hooks, barbs, flanges, partial or completely through-wall tee structures, or biological anchoring. Where multiple components are provided, reduction of the mitral valve annulus may be accomplished during initial deployment of the device, or by biological actuation during subsequent in-dwelling of the device.

Figure 2:
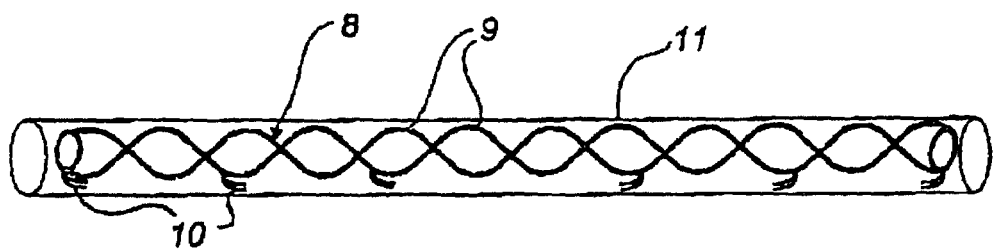
FIGS. 2–3 are schematic views of a first embodiment according to the present invention.
Figure 3:
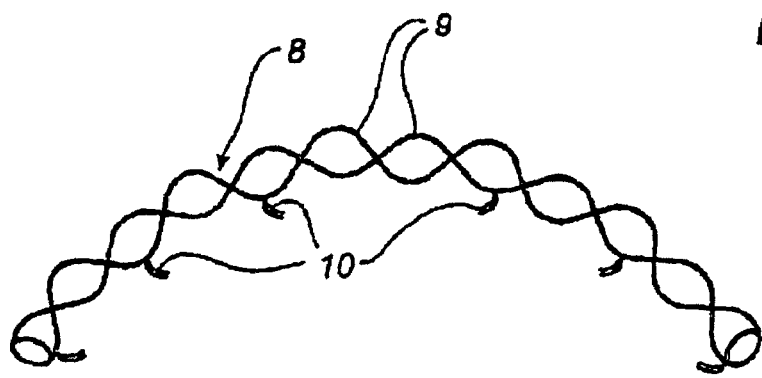

With respect to FIGS. 2 and 3, a device that experiences shortening during deployment is described as comprising an elongate body 8 made of memory metal, e.g. Nitinol, or other similar material which has a memory of an original shape, illustrated in FIG. 3, and which can be temporarily forced into another shape, illustrated in FIG. 2. Elongate body 8 comprises one, two or more memory metal strings 9 of helical or other shape so as to fit together and be able of to permit the movements described below. Along elongate body 8, plurality of hooks 10 are fastened so as to extend radially out therefrom. Hooks 10 are covered by a cover sheath 11 in FIG. 2.

Figure 4:
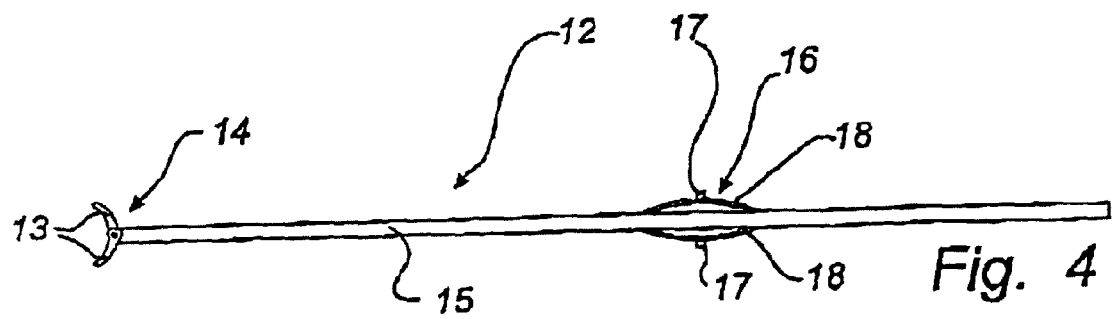
FIGS. 4–6 are schematic views illustrating an instrument that may be used when positioning the device of FIGS. 2–3 in the coronary sinus.

Elongate body 8 is forced into a stretched or extended state by means of stabilizing instrument 12 shown in FIG. 4. Instrument 12 has two arms 13 at distal end 14 of rod 15 and locking means 16 at proximal end of rod 15. The distance between the ends of rod 15 corresponds to the desired length of elongate body 8 when being inserted into coronary sinus 5.

Figure 5:
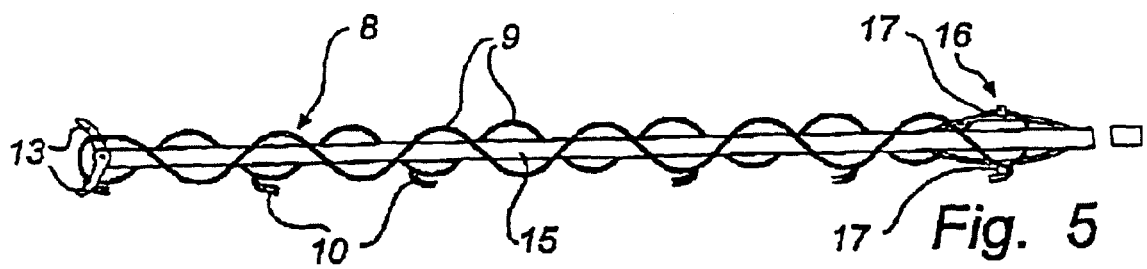
Figure 6:
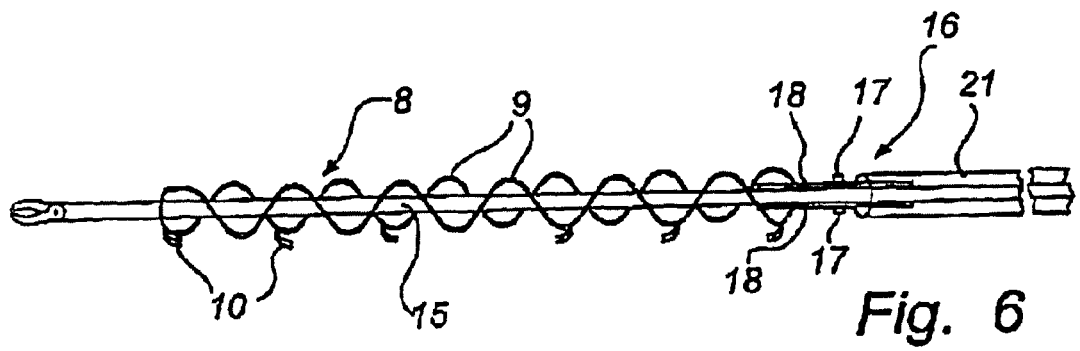

Arms 13 are free to move between the position shown in FIG. 4 and a position in alignment with rod 15, as shown in FIG. 6. Locking means 16 has two locking knobs 17, which are pressed radially outwards from rod 15 by two spring blades 18. Thus, elongated body 8 can be pushed over rod 15 of stabilizing instrument 12, then stretched between arms 13 and knobs 17, and finally locked in its stretched state on stabilizing instrument 12 between arms 13 and knobs 17, as illustrated in FIG. 5.

Rod 15 may be a metal wire which is relatively stiff between distal end 14 and locking means 16 but still so bendable that it will follow the shape of coronary sinus 5. Proximally of locking means 16 the metal wire of stabilizing instrument 11 is more pliable to be able to easily follow the bends of the veins.

The above-described elongate body 8 is positioned in the coronary sinus 5 in the following way:

An introduction sheath (not shown) of synthetic material may be used to get access to the venous system. Having reached access to the venous system, a long guiding wire (not shown) of metal is advanced through the introduction sheath and via the venous system to coronary sinus 5. This guiding wire is provided with X-ray distance markers so that the position of the guiding wire in coronary sinus 5 may be monitored.

Figure 8:
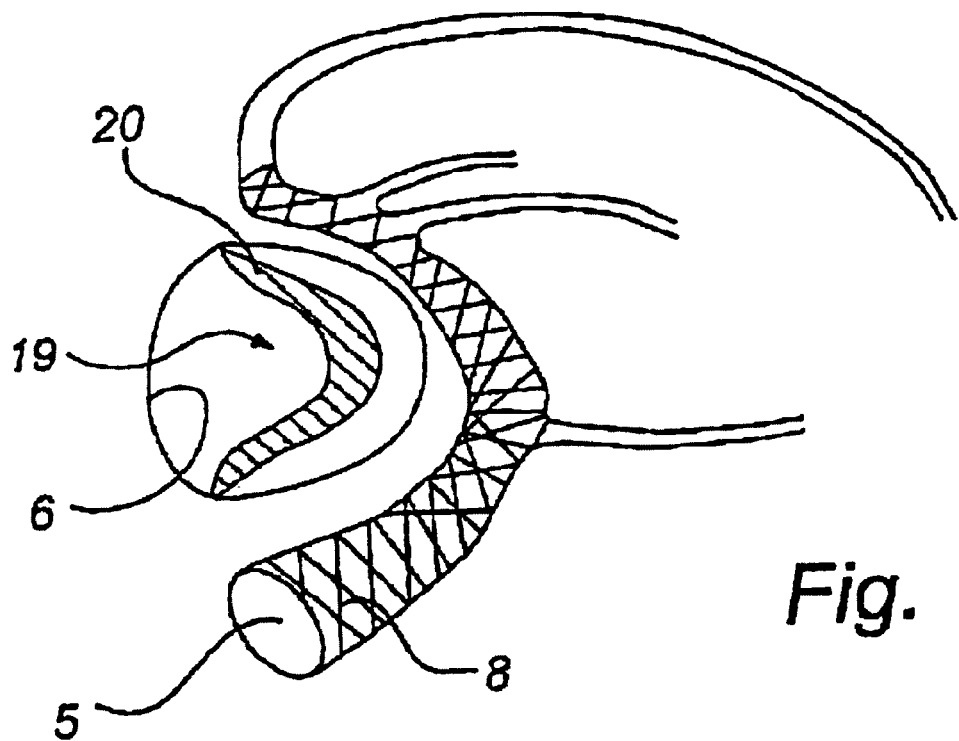
FIGS. 8–9 are schematic views illustrating the positioning of the device of FIGS. 2–3 in the coronary sinus.

Elongate body 8 is locked onto stabilizing instrument 12, as shown in FIG. 5, and introduced into long cover sheath 11 of synthetic material. This aggregate is then pushed through the introduction sheath and the venous system to coronary sinus 5 riding on the guiding wire. After exact positioning of elongate body 8 in coronary sinus 5, as illustrated in FIG. 8 where mitral valve 19 is shown having central gap 20, cover sheath 11 is retracted to expose elongate body 8 within coronary sinus 5. This maneuver allows hooks 10 on elongate body 8 to dig into the walls of coronary sinus 5 and into the heart. Elongate body 8 is still locked on to stabilizing instrument 12 such that hooks 10 engage the walls of coronary sinus 5 in the stretched or extended state of elongate body 8.

Figure 9:
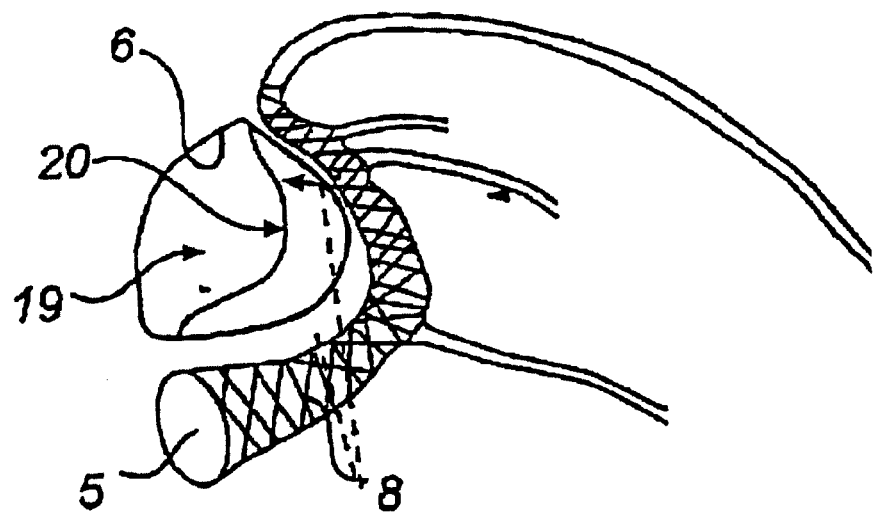

Catheter 12, shown in FIG. 6, is pushed forward on the guiding wire and rod 15, to release elongate body 8 from locking means 16 by pressing spring blades 18 toward rod 15. This movement releases knobs 17 as well as arms 13 from engagement with elongate body 8, which contracts elongate body 8 as illustrated in FIG. 9, thereby shortening the radius of curvature of coronary sinus 5. As a result, mitral valve annulus 6 shrinks moving the posterior part thereof forward (shown by arrows in FIG. 9). This movement reduces the circumference of mitral valve annulus 6 and thereby closes central gap 20.

Figure 7:
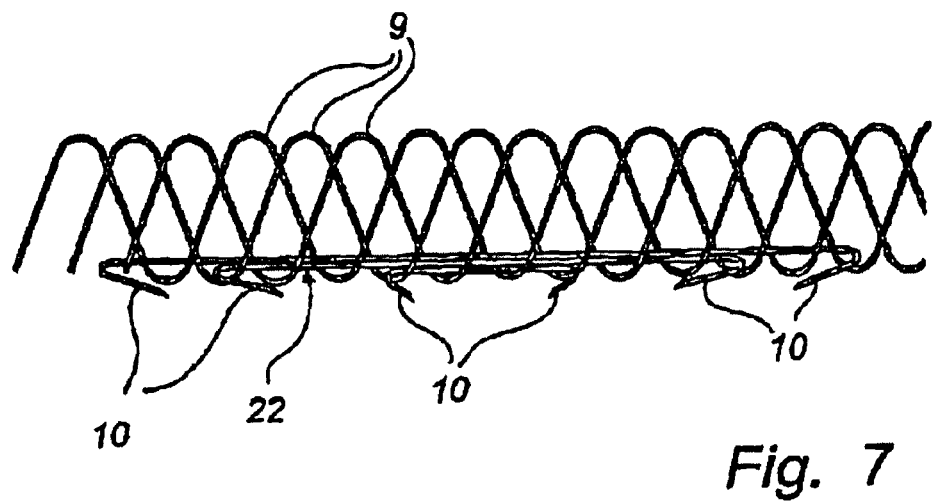
FIG. 7 is a partial, enlarged view of the first embodiment shown in FIG. 2.

FIG. 7 illustrates a part of an arrangement of wires 9 and hooks 10 along a peripheral part of elongate body 8, whereby elongate body 8 will be asymmetrically contracted resulting in a bending thereof when interconnecting parts 13 of at least some of hooks 10 are shortened to an original shape.

Figure 10:
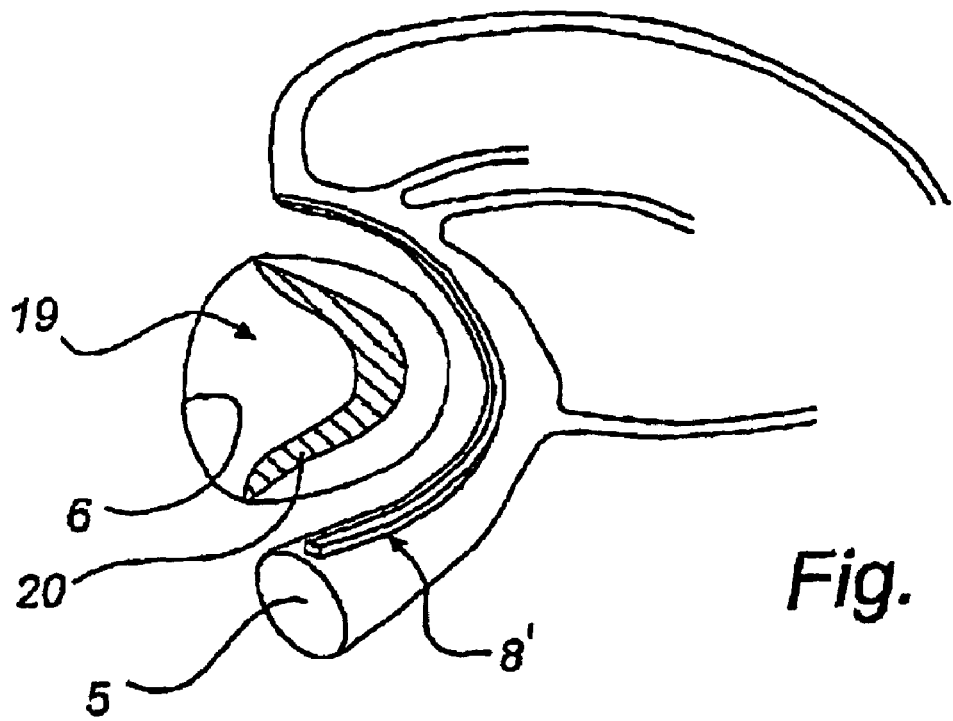
FIGS. 10–11 are schematic views illustrating the positioning of a solid U-shaped wire within the coronary sinus.
Figure 11:
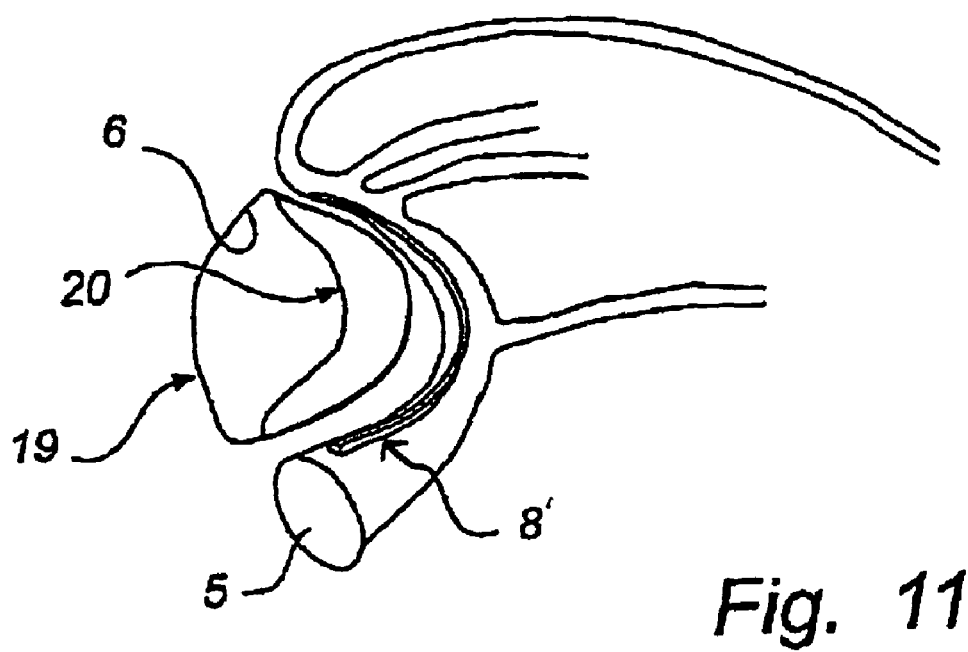

FIGS. 10 and 11 illustrate an alternative embodiment of an elongate body 8' which does not experience shortening during deployment. Elongate body 8' comprises a solid wire in the shape of an open U-shaped ring that will engage the wall of coronary sinus 5 most adjacent to mitral valve annulus 6 when inserted into coronary sinus 5. Elongate body 8' consists of a memory metal material which when reverting to its original shape will bend as illustrated in FIG. 11. The return of open ring 8' to its original shape may be initiated in several ways, as is obvious to one skilled in the art.

Further embodiments comprising two or more stent sections that are coupled by a system of wires and eyelets are described in co-pending U.S. patent application Ser. No. 09/775,677 ("the '677 application"), filed Feb. 5, 2001, U.S. Patent Application Publication No. 2001/0018611, which is incorporated herein by reference. In the embodiments described therein, individual proximal and distal stents are first deployed in the coronary sinus, and a cinch mechanism, illustratively comprising a wire and eyelets, is used to draw the proximal and distal stent sections towards one another, thereby reducing the circumference of the mitral valve annulus.

Referring now to FIG. 12, a further alternative embodiment is described, wherein the proximal stent section includes a flange that can be deployed to abut against the coronary ostium. Apparatus 56 comprises device 58 disposed within delivery sheath 60. Device 58 comprises proximal stent section 62 joined to distal stent section 64 via wire 66 and cinch mechanism 67. Proximal and distal stent sections 62 and 64 illustratively are self-expanding stents, but alternatively may comprise balloon expandable stents, coiled-sheet stents, or other type of stent.

Figure 12A:
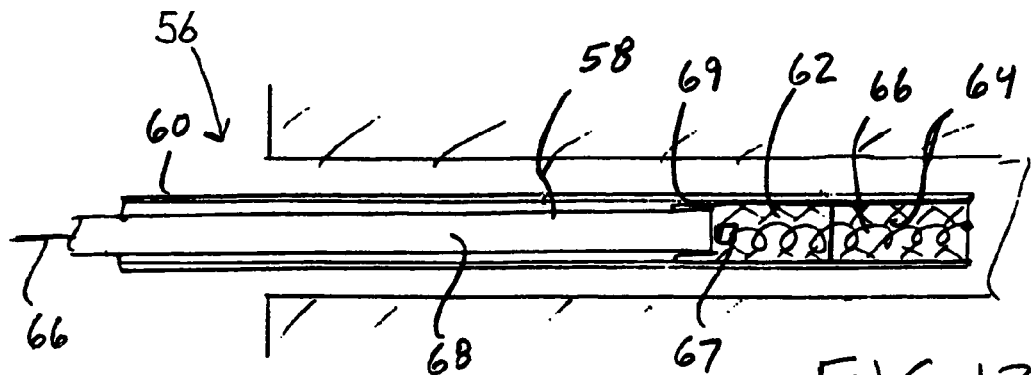
FIGS. 12A–12D illustrate an alternative embodiment comprising a deployable flange coupled to the proximal stent section.

Stents 62 and 64 are disposed within delivery sheath 60 with a distal end of push tube 68 contacting the proximal end of proximal stent section 62. Proximal stent section 62 comprises deployable flange 69. Deployable flange 69 is initially constrained within delivery sheath 60, as shown in FIG. 12A, and preferably comprises a shape memory material, e.g., Nitinol, so that flange 69 self-deploys to a predetermined shape upon retraction of delivery sheath 60.

Wire 66 and cinch mechanism 67 may comprise a combination of wires and eyelets as described in accordance with any of the embodiments in the '677 application, or any other arrangement that permits the wire to be tightened and locked into position, as will be apparent to one of ordinary skill. Wire 66 includes a proximal portion that remains outside of the patient's vessel for manipulation by a physician, and is configured to reduce the distance between proximal and distal stent sections 62 and 64.

Figure 12B:
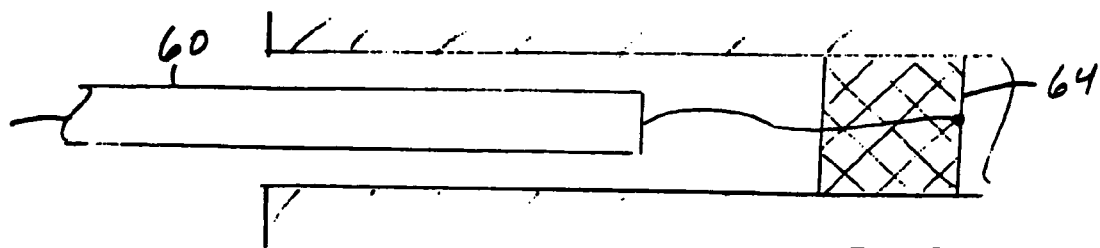

Apparatus 56 is navigated through the patient's vasculature with stents 62 and 64 in the contracted state and into coronary sinus C. The distal end of sheath 60 is disposed, under fluoroscopic guidance, at a suitable position within the coronary sinus, great cardiac vein, or adjacent vein. Push tube 68 is then urged distally to eject distal stent section 64 from within delivery sheath 60, thereby permitting distal stent section 64 to self-expand into engagement with the vessel wall, as shown in FIG. 12B.

Figure 12C:
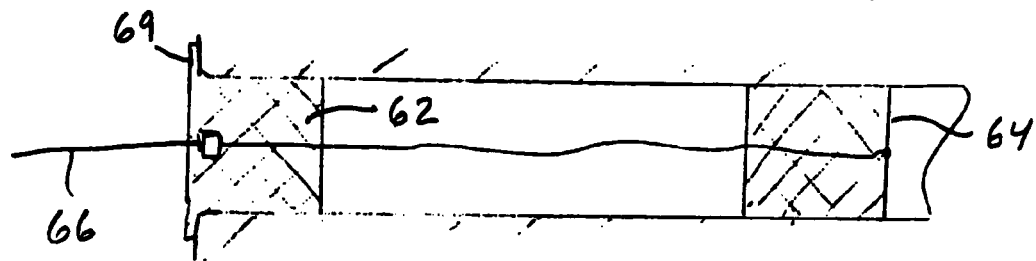

Delivery sheath 60 is then withdrawn proximally, under fluoroscopic guidance, until proximal stent 62 is situated extending from the coronary sinus. Push tube 68 is then held stationary while sheath 60 is further retracted, thus releasing proximal stent section 62. Once released from delivery sheath 60, proximal stent section 62 expands into engagement with the wall of the coronary sinus, and flange 69 abuts against the coronary ostium O, as shown in FIG. 12C.

Figure 12D:
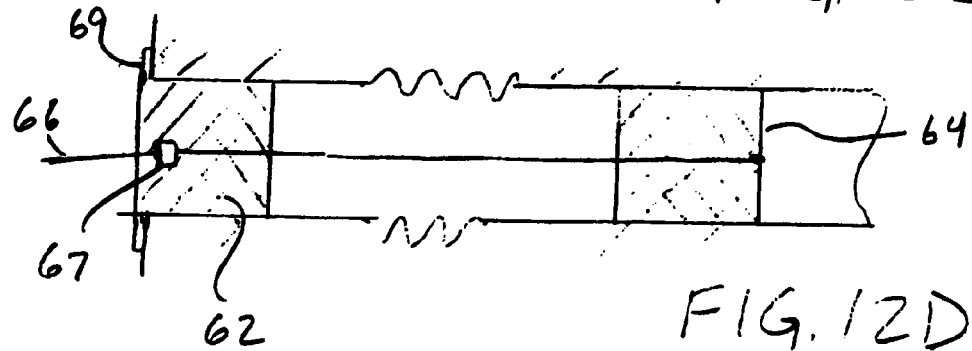

Delivery sheath 60 (and or push tube 68) may then be positioned against flange 69 of proximal stent section 62, and wire 66 retracted in the proximal direction to draw distal stent section 64 towards proximal stent section 62. As will of course be understood, distal stent section 64 is drawn towards proximal stent section 62 under fluoroscopic or other type of guidance, so that the degree of reduction in the mitral valve annulus may be assessed. As wire 66 is drawn proximally, cinch mechanism 67 prevents distal slipping of the wire. For example, wire 66 may include a series of grooves along its length that are successively captured in a V-shaped groove, a pall and ratchet mechanism, or other well-known mechanism that permits one-way motion. Catheter 60 and push tube 68 then may be removed, as shown in FIG. 12D.

Flange 69 may comprise a substantially circular shape-memory member, as illustrated, a plurality of wire members, e.g., manufactured using Nitinol, that self-deploy upon removal of sheath 60 and abut ostium O when proximally retracted, or other suitable shape.

Figure 13A:
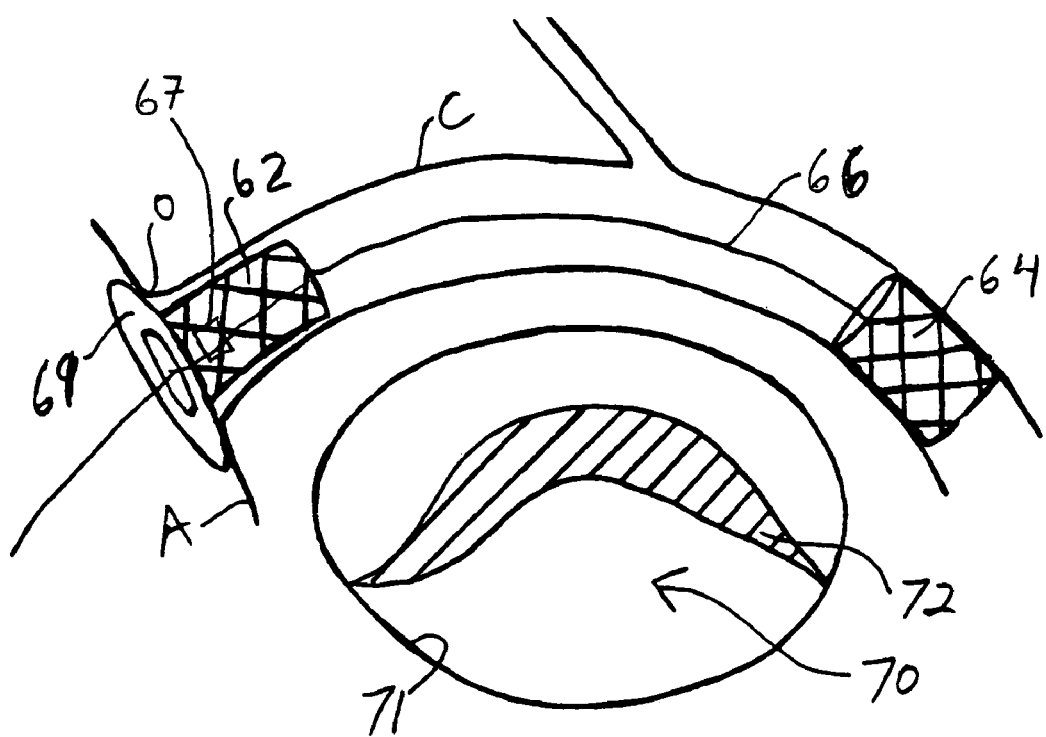
FIGS. 13A–13B illustrate deployment and actuation of the device of FIGS. 12A–12C.

Referring to FIG. 13, a preferred method for using apparatus 56 of FIG. 12 to close a central gap 72 of mitral valve 70 is described. In FIG. 13A, proximal and distal stent sections 62 and 64 are deployed in the coronary sinus so that flange 69 of proximal stent section 62 engages coronary ostium O. Distal stent section 64 is disposed at such a distance apart from proximal stent section 62 that the two stent sections apply a compressive force upon mitral valve 70 when wire 66 and cinch 67 are actuated.

Figure 13B:
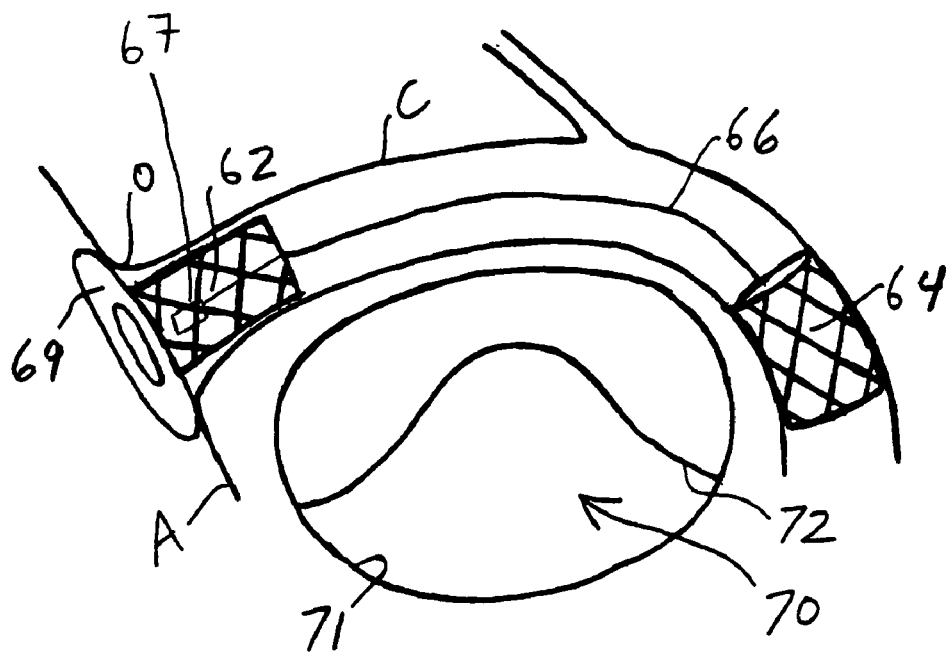

In FIG. 13B, cinch 67 is actuated from the proximal end to reduce the distance between proximal and distal stent section 62 and 64, e.g., as described hereinabove. When wire 66 and cinch mechanism 67 are actuated, distal stent section 64 is pulled in a proximal direction and proximal stent section 62 is pulled in a distal direction until flange 69 abuts coronary ostium O. The reduction in distance between proximal and distal stent sections 62 and 64 reduces the circumference of mitral valve annulus 71 and thereby closes gap 72. Flange 69 provides a secure anchor point that prevents further distally-directed movement of proximal stent section 62, and reduces shear stresses applied to the proximal portion of the coronary sinus.

Referring now to FIG. 14, a further aspect of the present invention is described, in which the distal stent section of the embodiment of FIG. 12 is replaced with an anchor that is disposed within or through the myocardium. As will be appreciated, this feature of the device of the present invention may be used either separately or in conjunction with the flange feature described hereinabove. Device 90 comprises proximal stent section 92 coupled by wire 94 and cinch mechanism 95 to distal anchor 96. Proximal stent section 92 may include flange 93. Optional coil section 98 extends distally from proximal stent section 92 to distal anchor 96, and serves to distribute compressive forces created by wire 94 to a larger area of the venous vessel wall.

Device 90 is loaded into delivery apparatus 100 comprising curved stylet 102, push wire 104 and delivery sheath 106. Curved stylet 102 preferably comprises a shape memory alloy capable of being straightened, but adopting a curved shape when extended beyond a distal end of delivery sheath 106. Curved stylet 102 includes sharpened distal tip 101 capable of piercing the left ventricular myocardium, and is disposed in lumen 105 of delivery sheath. Push wire 104 is slidably disposed in lumen 103 of curved stylet 102, and may be advanced distally to eject distal anchor 96 into the left ventricular myocardium or the left ventricle.

Figure 14A:
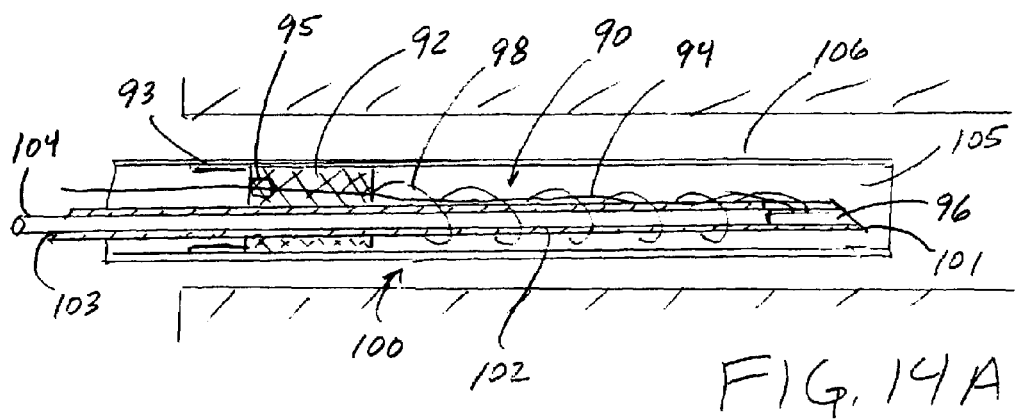
FIGS. 14A–14C illustrate an alternative embodiment of the device of the present invention having a distal anchor.

As depicted in FIG. 14A, distal anchor comprises a Tee-shaped bar to which wire 94 is coupled. Optional coil section 98 also may be coupled to distal anchor 96, and is contracted around curved stylet 102 when device 90 is loaded into delivery sheath 106. Distal anchor 96 is disposed within lumen 103 of curved stylet so that wire 94 and coil section 98 exit through lateral slot 107 in the stylet. Push wire 104 is disposed in lumen 103 of stylet 102 abutting against the proximal face of distal anchor 96.

Figure 14B:
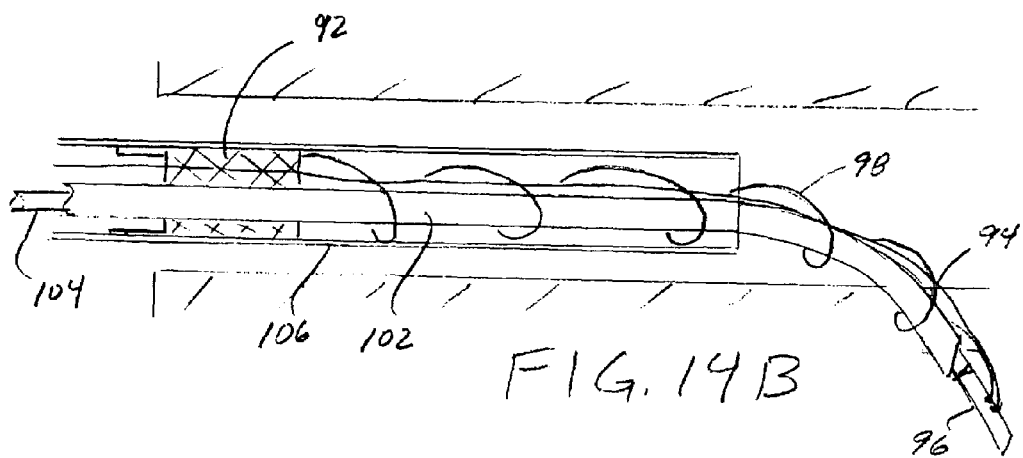

In FIG. 14A, device 90 is shown loaded into delivery apparatus 100. Delivery apparatus 100 has been disposed in the coronary sinus using conventional guidance and visualization techniques. The distal end of delivery apparatus 100 is advanced into the coronary venous vasculature to a desired location, and then stylet 102 is advanced distally beyond the end of delivery sheath 106, thereby causing the stylet to regain its curved shape. Further advancement of stylet 102 causes the distal end of the stylet to pierce the coronary vein and extend into the left ventricular myocardium. Push rod 104 is then advanced distally to eject distal anchor 96 into the myocardium, or within the left ventricle, as shown in FIG. 14B.

Figure 14C:
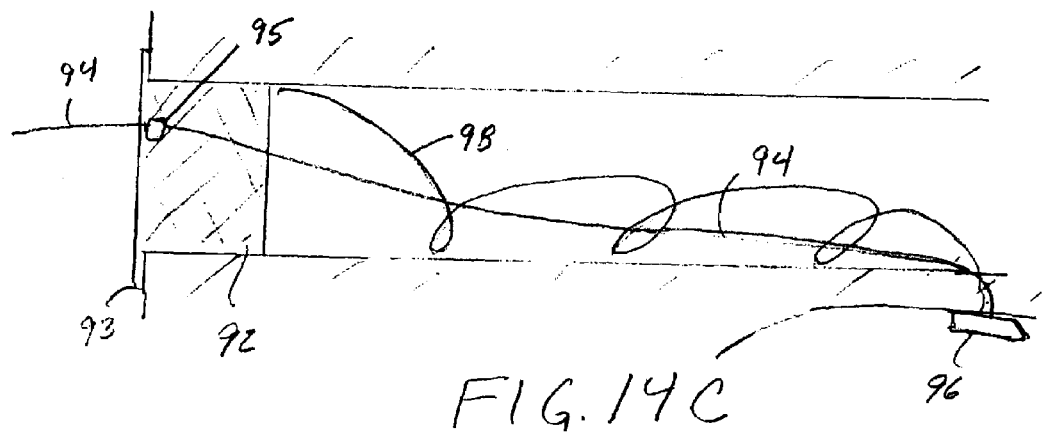

Stylet 102 and push wire 104 are then withdrawn, and delivery sheath 106 is retracted until the proximal stent section is disposed extending out of the coronary ostium. By selection of the length of wire 94 fed through cinch mechanism 95, proximal stent section 92 may be deployed simply by retracting delivery sheath 106, because distal anchor 96 and wire 94 will prevent further proximal movement of proximal stent section 92. In any event, when proximal stent section 92 is released from delivery sheath 106, it self-expands to engage the vessel wall while flange 93 contacts the coronary ostium, as shown in FIG. 14C.

The proximal end of proximal wire 94 extends through lumen 105 of delivery sheath 106 and may be manipulated by a physician. As in the previous embodiment, once the proximal stent section is deployed, wire 94 may be pulled proximally, with cinch mechanism 95 taking up any slack. The distance between distal anchor 96 and proximal stent section 92 may therefore be reduced a desired amount, causing a corresponding reduction in the circumference of the mitral valve annulus. Optional coil section 98, if present, assists in redistributing the compressive forces applied by wire 94 to the interior surface of the venous vessel.

Figure 15A:
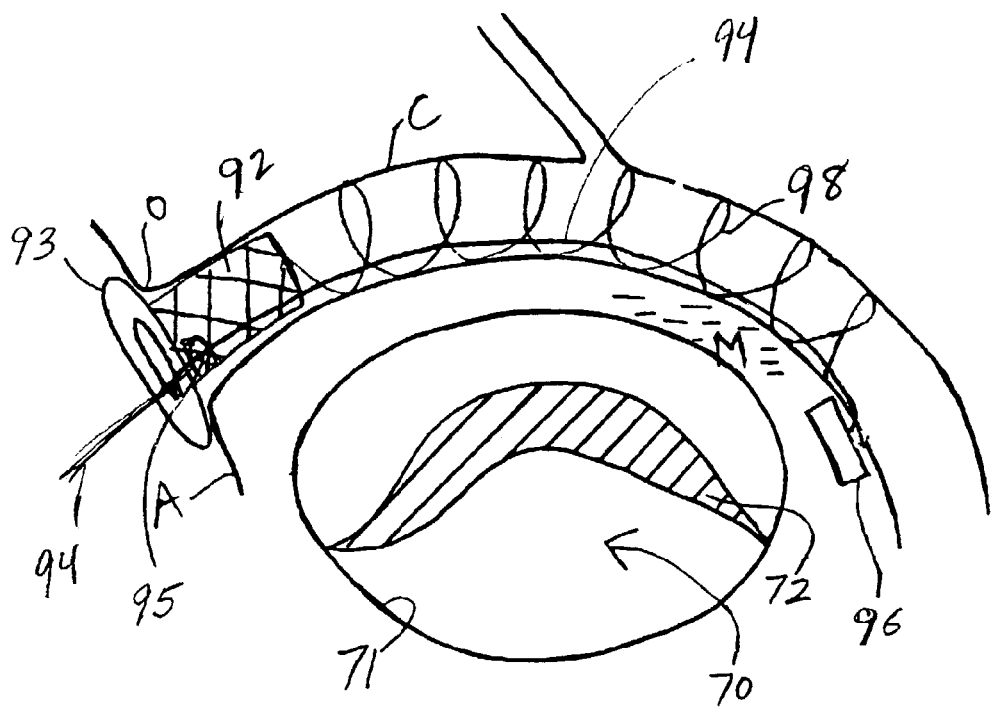
FIGS. 15A–15B illustrate deployment and actuation of the device of FIGS. 14A–14C.
Figure 15B:
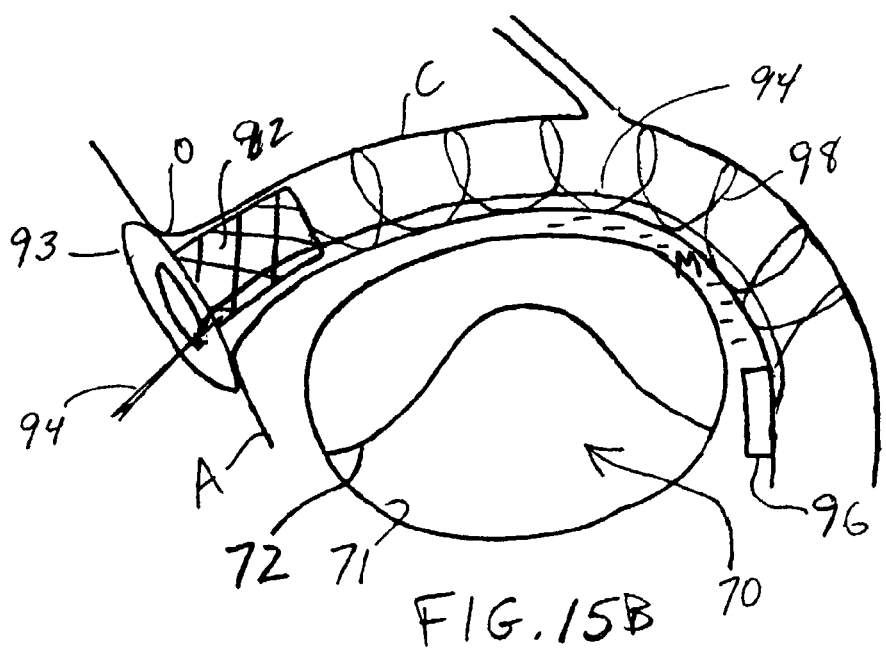

Referring to FIGS. 15A and 15B, device 90 of FIG. 14 is illustrated in a deployed state to treat mitral insufficiency. Flange 93 is deployed abutting coronary ostium O, e.g., within right atrium A. Proximal stent section 92 and optional coil section 98 are deployed within the coronary sinus and great cardiac vein C. Distal anchor 96 is disposed within myocardium M, or alternatively, may extend into the left ventricle or another suitable region, as will be obvious to those skilled in the art. It should further be appreciated to those skilled in the art that while anchor 96 is illustrated as a cylindrical bar, it may comprise square, circular or other configurations, e.g., a plurality of barbs.

The proximal end of wire 94 extends through cinch mechanism 95 and is manipulated to impose tension on wire 94, thereby reducing the distance between proximal stent section 92 and distal anchor 96. This in turn reduces the circumference of coronary sinus C accordingly, as shown in FIG. 15B. Upon completion of the procedure, i.e., when gap 72 is sufficiently closed, apparatus 100 is removed from the patient's vessel.

Advantageously, the use of distal anchor 96 is expected to reduce the shear stress imposed on coronary sinus C relative to the use of a proximal stent section alone as described for the embodiment of FIGS. 12 and 13.

Figure 16A:
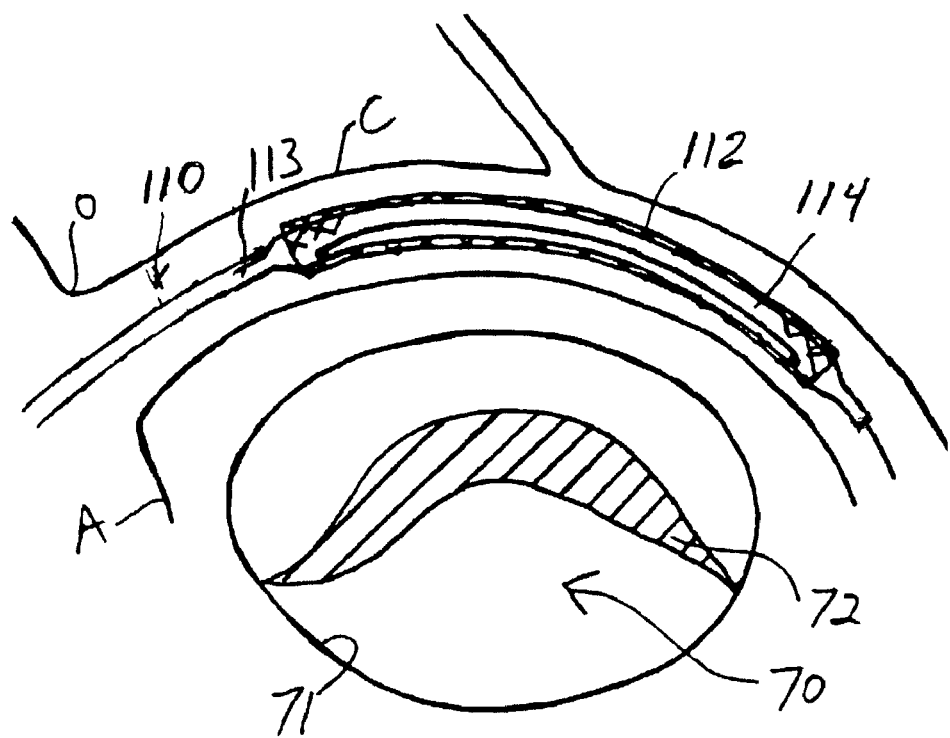
FIGS. 16A–16B illustrate another alternative embodiment of the device of the present invention comprising a balloon-expandable device that is deployed to a curved shape.

Referring now to FIGS. 16 and 17, another embodiment of a device suitable for repairing mitral valve insufficiency is described. In this embodiment, device 110 comprises a balloon expandable stent 112, which may be tapered along its length. Stent 112 is disposed on balloon 114 at the distal region of balloon catheter 113. Balloon 114 is capable of assuming a curved shape when inflated. As depicted in FIG. 16A, stent 112 and balloon catheter 113 are disposed in the patient's coronary sinus through the coronary ostium.

Once the position of stent 112 is determined, for example, by fluoroscopy, balloon 114 is inflated via to expand balloon 114 to its predetermined curved shape. Inflation of balloon 114 causes stent 112 to be plastically deformed in accordance with the predetermined shape of balloon 114. As will be of course be appreciated, the degree of mitral valve regurgitation may be monitored during the step of inflating balloon 114, so that stent 112 applies only so much compressive load on the mitral valve annulus as is required to reduce the regurgitation to a clinically acceptable level. Catheter 113 is removed from the patient's vessel upon completion of the stenting procedure.

Figure 16B:
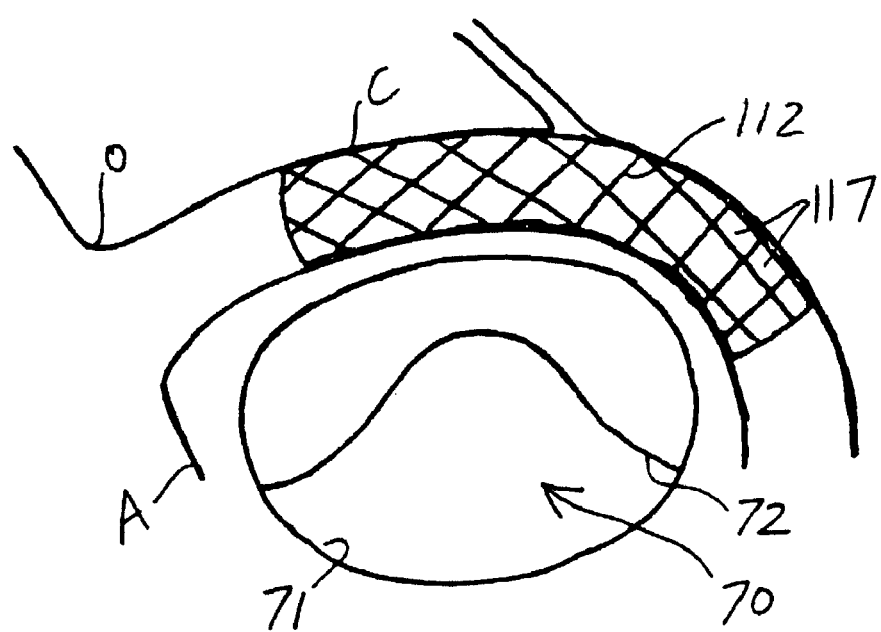
Figure 17A:
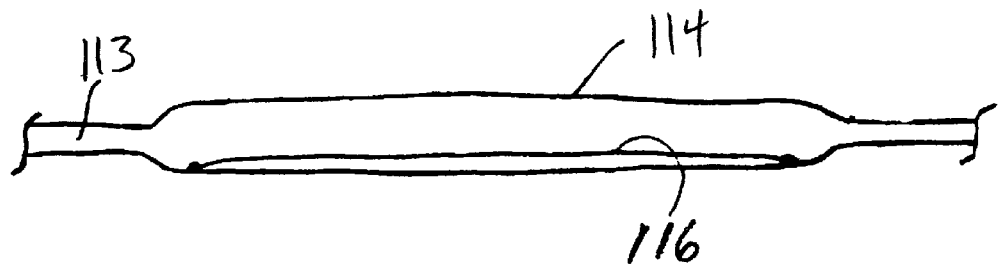
FIGS. 17A–17B illustrate a balloon that deploys to a predetermined curved shape.
Figure 17B:
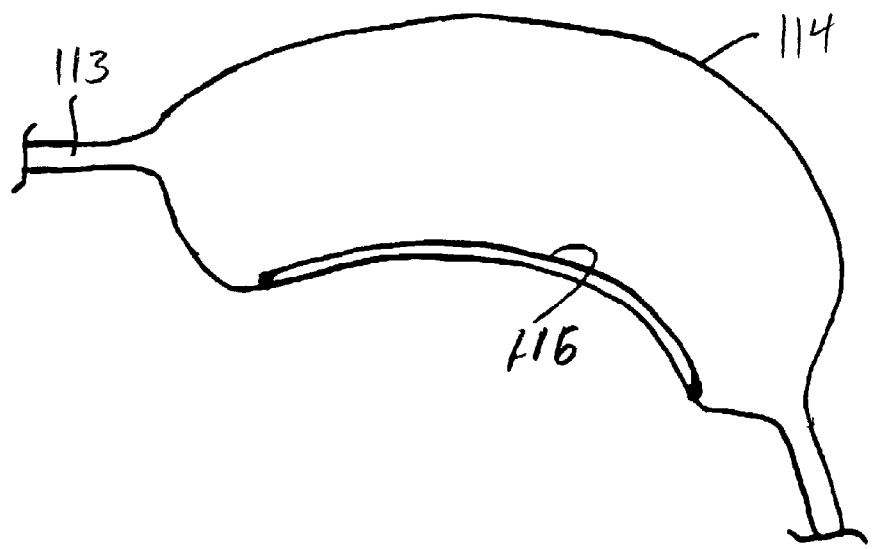

Referring to FIGS. 17A and 17B, the distal region of a balloon catheter suitable for use in the embodiment of FIG. 16 is described. Balloon catheter 113 has proximal and distal ends, and comprises balloon 114, and inflation lumen and guidewire lumens, as is per se known. In accordance with the principles of the present invention, balloon 114 includes an anchor element 116, such as a strand of wire, affixed to its interior surface, so that when the balloon is inflated, it adopts a predetermined shape, as shown in FIG. 17B. Anchor element 116 may comprise a radiopaque material or radiopaque coating to facilitate proper positioning of stent 112 within coronary sinus C. When balloon 114 is deflated, the balloon assumes a straight configuration, shown in FIG. 17A, thus permitting stent 112 to be crimped to its outer surface.

In an alternative embodiment of the device of FIGS. 16–17, anchor element 116 may be omitted and balloon 114 may be pre-shrunk on one side, thereby causing the balloon to deploy to the shape depicted in FIG. 17B. In yet another embodiment, the configuration of cells 117 of stent 112 may be varied to encourage the stent to assume a convex shape upon deployment. For example, the side of the stent adjacent mitral valve annulus 71 may expand less than the side of the stent opposing the mitral valve annulus, thereby imparting a convex curvature upon the stent, as shown in FIG. 16B.

To ensure proper alignment of stent 112 within the coronary sinus prior to deployment of the stent, an intravascular ultrasound transducer or, alternatively, radiopaque marker bands may be used to align the correct side of the stent adjacent the mitral valve annulus. The use of such imaging modalities are described, for example, in U.S. patent application Ser. No. 09/916,394 ("the '394 application"), which is U.S. Patent Application Publication No. 2002/0019660, hereby incorporated by reference in its entirety. Additionally, further techniques for providing a curved stent in accordance with methods of FIGS. 16–17 also are described in the '394 application.

Figure 18A:
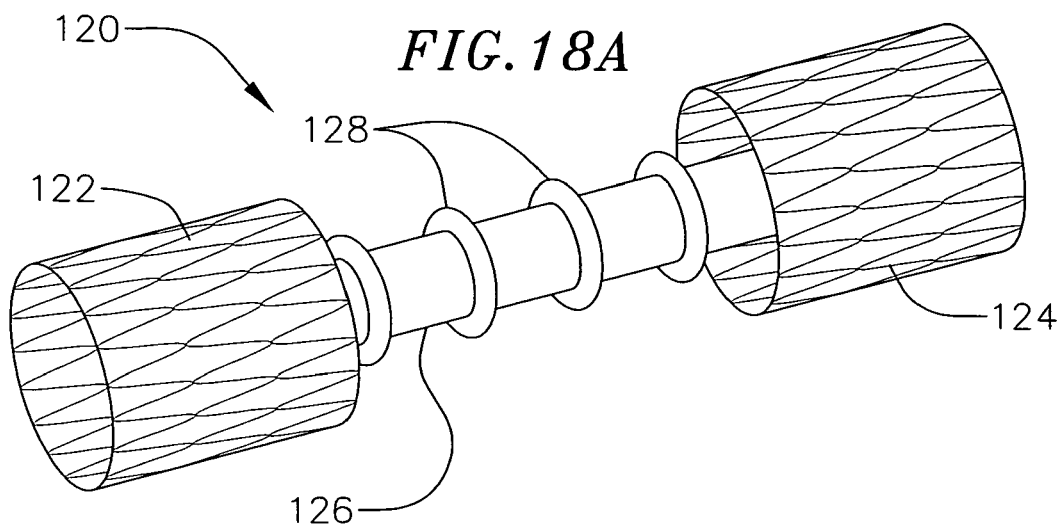
FIGS. 18A–18C are perspective and side views of a further alternative embodiment of a device of the present invention.
Figure 18B:
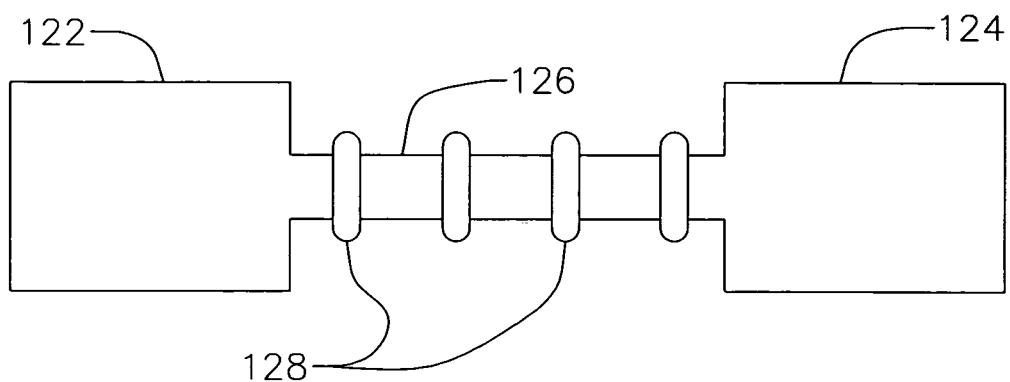
Figure 18C:
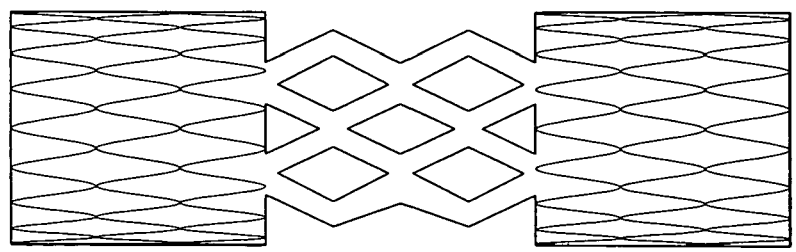

Referring now to FIGS. 18A–19C, another alternative embodiment of the present invention is described, in which the device comprises proximal and distal stent sections joined by a central section capable of undergoing foreshortening. Device 120 comprises proximal stent section 122, distal stent section 124 and central section 126. Further in accordance with the principles of the present invention, device 120 includes one or more biodegradable structures 128, such as sutures, disposed on central section 126 to retain that section in the contracted shape for a predetermined period after placement of the device in a patient's vessel. In FIG. 18A, device 120 is depicted with its proximal and distal stent sections radially expanded, but with central section 126 restrained in the contracted position. FIG. 18B depicts device 120 with all three stent sections contracted as if disposed in a delivery catheter. FIG. 18C shows all three stent sections fully expanded.

In a preferred embodiment, all three sections are integrally formed from a single shape memory alloy tube, e.g., by laser cutting. The stent sections then are processed, using known techniques, to form a self-expanding unit. Device 120 has a contracted delivery configuration, wherein the device is radially contracted within a delivery sheath, and a deployed expanded configuration, wherein at least the proximal and distal sections self-expand to engage the interior surface of the coronary sinus or adjoining veins. Further in accordance with the present invention, the biodegradable structures may be designed to biodegrade simultaneously or at selected intervals.

Unlike the preceding embodiments, which may include either a proximal flange, distal anchor, or both, and which rely upon drawing the proximal and distal stent sections together at the time of deploying the device, this embodiment of the present invention permits the proximal and distal stent sections 122 and 124 to become biologically anchored in the venous vasculature before those sections are drawn together by expansion of central section 126 to impose a compressive load on the mitral valve annulus.

In particular, as depicted in FIGS. 19A–19D, device 120 is loaded into delivery sheath 121 and positioned within the patient's coronary sinus. The device is then ejected from the delivery sheath, so that the proximal and distal stent sections 122 and 124 radially expand into engagement with the vessel wall. At the time of deployment, central section 126 is retained in a contracted state by biodegradable structures 128, illustratively biodegradable sutures, e.g., a poly-glycol lactide strand or VICREL suture, offered by Ethicon, Inc., New Brunswick, N.J., USA.

Figure 19A:
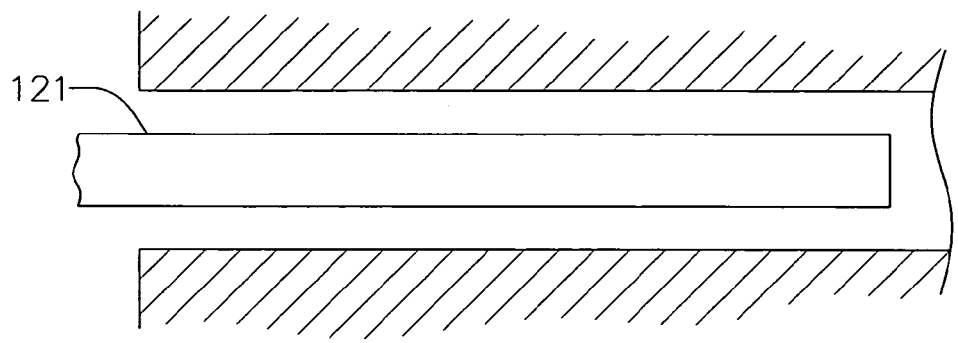
FIGS. 19A–19D illustrate deployment of the device depicted in FIGS. 18A–18B.
Figure 19B:
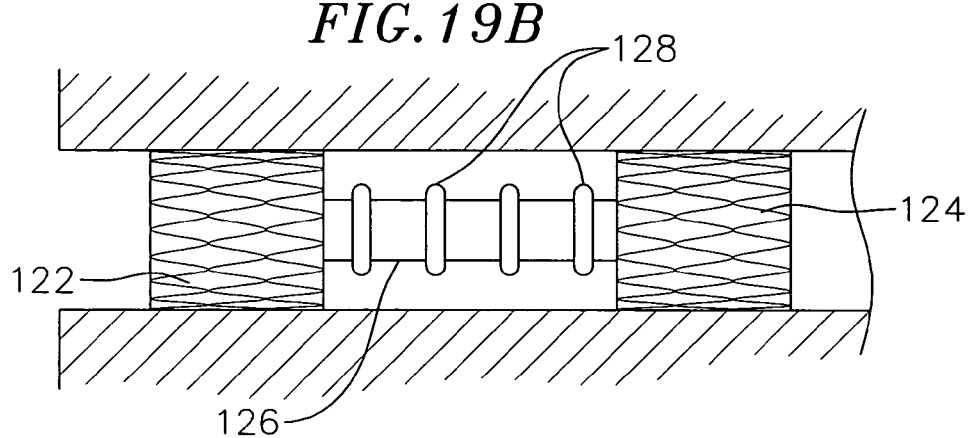
Figure 19C:
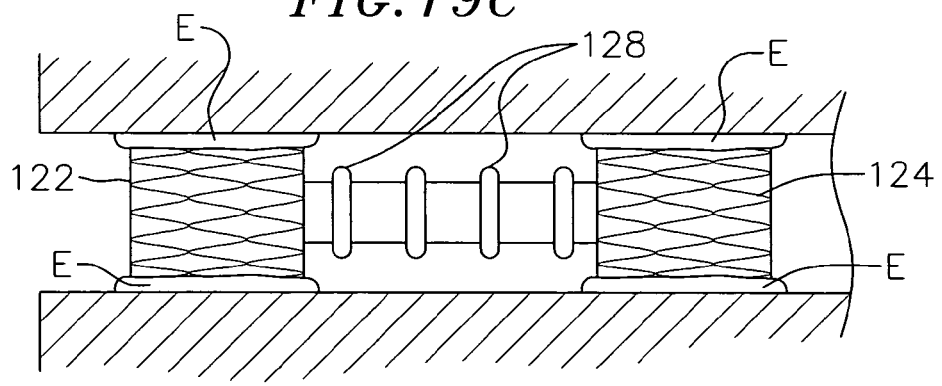

Over the course of several weeks to months, the proximal and distal stent sections 122 and 124 will endothelialize, i.e., the vessel endothelium will form a layer E that extends through the apertures in the proximal and distal stent sections and causes those stent sections to become biologically anchored to the vessel wall, as depicted in FIG. 19C. This phenomenon may be further enhanced by the use of a copper layer on the proximal and distal stent sections, as this element is known to cause an aggressive inflammatory reaction. Other techniques for enhancing an inflammatory reaction, such as coatings or layers, will be apparent to those skilled in the art.

Figure 19D:
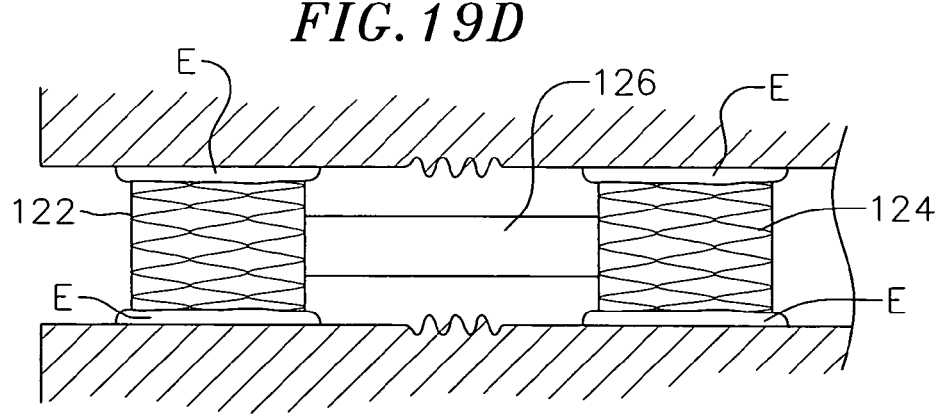

Over the course of several weeks to months, and preferably after the proximal and distal stent sections have become anchored in the vessel, biodegradable structures 128 that retain central section 126 in the contracted state will biodegrade. Eventually, the self-expanding force of the central section will cause the biodegradable structures to break, and release central section 126 to expand. Because central section 126 is designed to shorten as it expands radially, it causes the proximal and distal stent sections 122 and 124 of device 120 to be drawn towards one another, as shown in FIG. 19D. The compressive force created by expansion of central section 126 thereby compressively loads, and thus remodels, the mitral valve annulus, as depicted.

As suggested hereinabove, biodegradable structures 128 may be designed to rupture simultaneously, or alternatively, at selected intervals over a prolonged period of several months or more. In this manner, progressive remodeling of the mitral valve annulus may be accomplished over a gradual period, without additional interventional procedures. In addition, because the collateral drainage paths exist for blood entering the coronary sinus, it is expected that the device will accomplish its objective even if it results in gradual total occlusion of the coronary sinus.

Figure 20A:
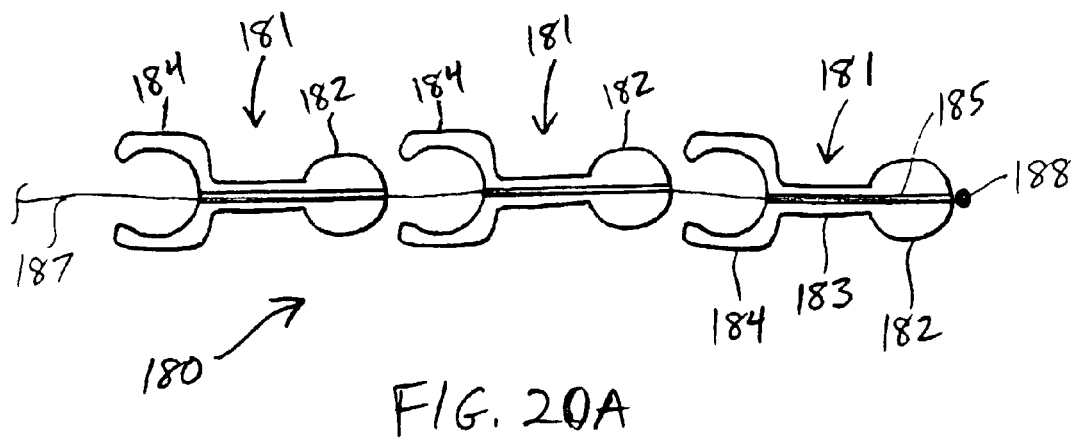
FIGS. 20–22 illustrate a still further alternative embodiment of the present invention comprising a plurality of interconnected segments and deployment thereof.
Figure 20B:
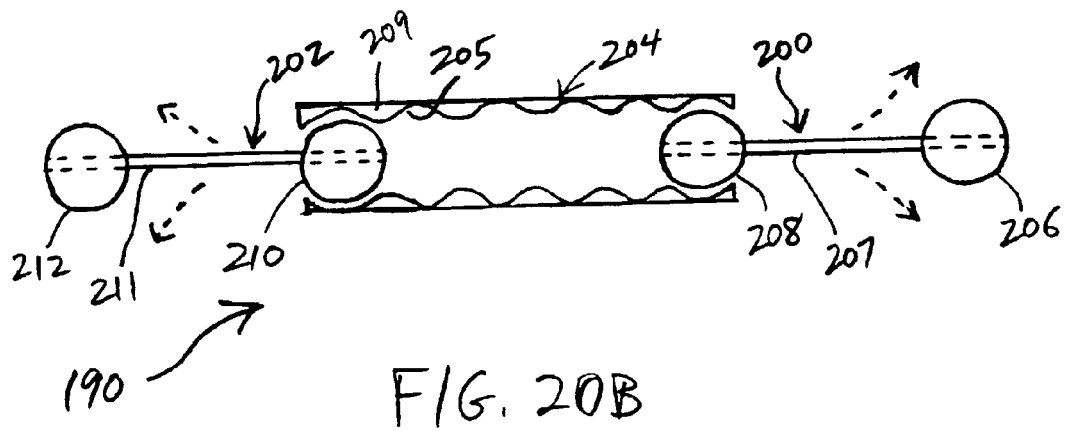

Referring now to FIGS. 20A–20B, another alternative embodiment of the present invention is described. In FIG. 20A, apparatus 180 comprises a plurality of interlocking segments 181. Each interlocking segment 181 preferably comprises a proximal section having socket 184, a distal section having ball 182, and a central section 183 extending therebetween. Each interlocking segment 181 further comprises lumen 185 configured to permit cinch wire 187 to pass through lumen 185. Cinch wire 187 having proximal and distal ends preferably comprises ball 188 affixed to the distal end so that ball 188 engages a distalmost interlocking segment 181 when retracted proximally. The retraction of cinch wire 187 enables a ball 182 to interlock with a socket 184 of an adjacent segment 181.

Apparatus 180 of FIG. 20A preferably is used in combination with apparatus 190 of FIG. 20B. A preferred use of apparatus 180 and 190 in combination is described in FIG. 22 hereinbelow. Apparatus 190 comprises proximal ball segment 202, distal ball segment 200, and connecting segment 204 having a plurality of sockets 205 separated by humps 209. Proximal ball segment 202 comprises proximal and distal ball segments 212 and 210, respectively, each having lumens extending therethrough, and hollow rod 211 extending therebetween. Similarly, distal ball segment 200 comprises proximal and distal balls 208 and 206, respectively, each having lumens extending therethrough, and hollow rod 207 extending therebetween. Distal ball 210 of proximal segment 202 initially is configured to engage the most proximal socket 205 within connecting segment 204, while proximal ball 208 of distal segment 200 initially is configured to engage a distalmost socket 205.

Figure 21A:
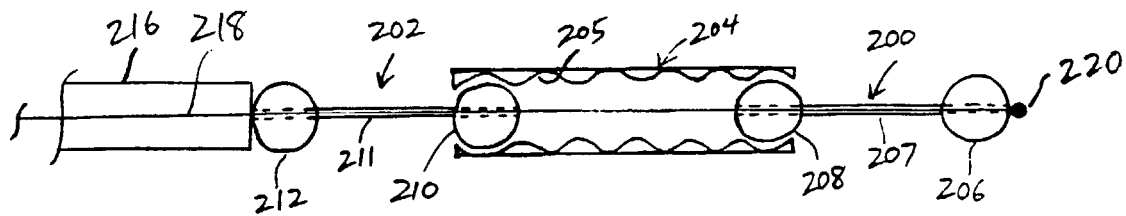

Proximal and distal ball segments 202 and 200 are capable of relative rotational and telescoping movement. Such movement may be achieved using a cinch wire configured to pass through each segment 200 and 202, as shown in FIG. 21A. In FIG. 21A, cinch wire 218 comprises distal ball 220 that is larger than a lumen of hollow rod 207 and is configured to abut distal ball 206 when a proximal end of cinch wire 218 is retracted proximally. Cinch wire 218 preferably is used in combination with push tube 216 that may stabilize or distally advance proximal segment 202.

Figure 21B:
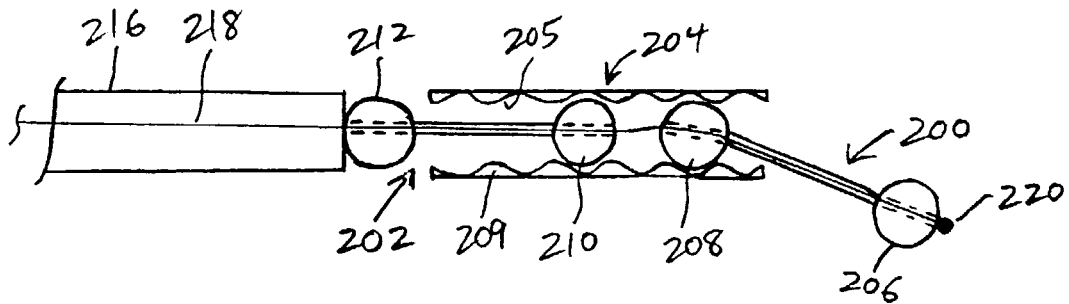

By varying the maneuvers of push tube 216 and cinch wire 218, a range of telescoping and rotational motions between proximal and distal segments 202 and 200 may be achieved, as shown in FIG. 21B. In FIG. 21B, a push force applied to ball 212 allows ball 210 to overcome the resistive forces provided by hump 209. As illustrated, the push force applied to ball 212 has advanced proximal segment 202 by two sockets relative to distal segment 200. Also, as shown in FIG. 21B, distal segment 200 has been retracted by one socket with respect to proximal segment 202, e.g., by proximally retracting cinch wire 218. Ball 208 also has been rotated at an angle, which in turn rotates distal segment 200 with respect to proximal segment 202.

Figure 21C:
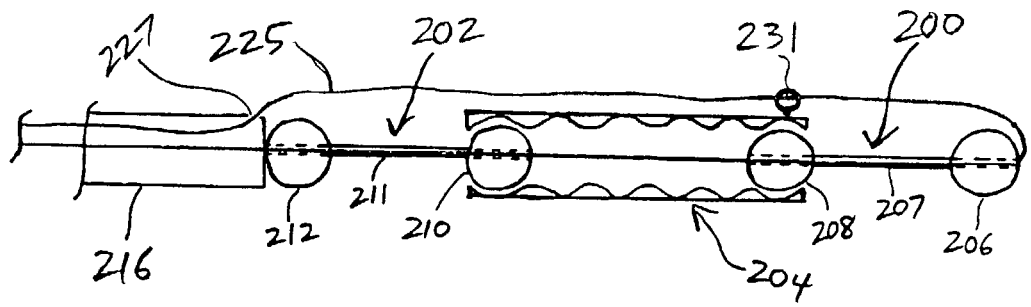

Referring to FIG. 21C, an alternative method for providing relative telescoping and rotational motion for apparatus 190 of FIG. 20B is described. Apparatus 190 further comprises push tube 216 and wire loop 225. Wire loop 225 extends through a lumen within proximal and distal segments 202 and 200, then loops around the distal end of distal segment 200 and back into opening 227 of push tube 216. A physician then may manipulate a proximal portion of wire loop 225 to provide a range of telescoping or rotational motions between proximal and distal segments 202 and 200. At least one hook or eyelet 231 may be coupled to an exterior surface of connecting segment 204 to serve as a guide for wire 225, and to facilitate controlled actuation of proximal and distal segments 202 and 200.

Figure 22:
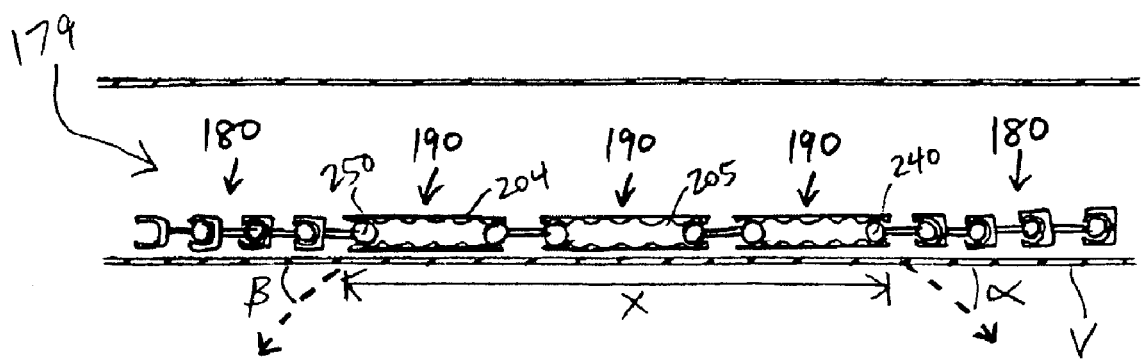

Referring now to FIG. 22, a combination of apparatus 180 and apparatus 190 are used to provide a range of motion within vessel V, e.g., the coronary sinus. As described hereinabove, the present invention aims to treat mitral insufficiency by shortening the radius of curvature of the coronary sinus, which in turn applies a compressive force upon the mitral valve. In FIG. 22, the combination of apparatus 180 and apparatus 190 first may engage a wall of vessel V, e.g., via barbs or hooks (not shown) affixed to apparatus 180 and 190, and then the relative telescoping or rotational motion of segments may be used to bend vessel V to apply a compressive load on the mitral valve annulus.

In a preferred embodiment, mitral insufficiency apparatus 179 comprises a proximal and distal section comprising apparatus 180, and a plurality of sections comprising apparatus 190 disposed therebetween. Cinch wire 218 and push tube 216 of FIG. 21 preferably are used to manipulate relative rotational and telescopic motion of all of the components. In a first preferred step, the balls of apparatus 180 are coupled to their respective sockets, e.g., by proximally retracting cinch wire 218. Then, in a next step, balls 240 and 250 which connect apparatus 180 to apparatus 190 are rotated within sockets of connective segment 204 to allow apparatus 180 to be angled relative to apparatus 190 by angles α and β, as illustrated in FIG. 22. This in turn applies a desired compressive load on the mitral valve annulus. Then, in a final step, the balls of apparatus 190 may be advanced incrementally in a longitudinal direction within sockets 205 of connective segments 204 to reduce distance X. When vessel V is the coronary sinus, reducing the distance X will apply a compressive force to the mitral valve to treat mitral insufficiency.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. An apparatus for treating mitral annulus dilatation of a heart, the apparatus comprising:
    a proximal anchor configured to be positioned in and fixed in the heart;
    a distal anchor configured to be positioned in and fixed in the heart distally of the proximal anchor; and
    a drawing member joined to the distal anchor and extending proximally from the distal anchor through a coronary sinus of the heart to the proximal anchor to draw the distal anchor towards the proximal anchor;
    wherein, in a first position, the proximal and distal anchors are configured to be fixed in the heart at a first distance apart from each other and the drawing member extends proximally of the proximal anchor and, in a second position, the proximal and distal anchors are configured to be fixed in the heart at a second distance closer together than in the first position.

2. The apparatus of claim 1 wherein the proximal anchor comprises a proximal stent section and the distal anchor comprises a distal stent section.

3. The apparatus of claim 2 wherein the proximal and distal stent sections are expandable from a reduced size configuration to an expanded configuration.

4. The apparatus of claim 1, wherein the drawing member is maneuverable from outside the vein system.

5. The apparatus of claim 1, wherein the drawing member is secured to the proximal anchor in the second position.

6. The apparatus of claim 1, wherein the drawing member is slidable relative to the proximal anchor.

7. The apparatus of claim 1, wherein the drawing member is a wire.

* * * * *

UNITED STATES PATENT AND TRADEMARK OFFICE
CERTIFICATE OF CORRECTION

PATENT NO. : 6,997,951 B2
DATED : February 14, 2006
INVENTOR(S) : Solem et al.

It is certified that error appears in the above-identified patent and that said Letters Patent is hereby corrected as shown below:

<u>Title page,</u>
Item [75], Inventors, after "Per-Ola Kimblad, Lund (SE);" delete "Randolf van Oepen, Tubingen (DE); Bodo Quint, Rottenburg-Seebronn (DE); Gerd Seibold, Ammerbuch (DE); Kenneth J. Michlitsch, Livermore, CA (US); Suk-Woo Ha, Langwiesen (CH); Karl-Ludwig Eckert, Marthalen, (CH); Ib Joergensen, Haigerloch (DE); Stevan Nielsen, Rottenberg (DE)".

Signed and Sealed this

Thirteenth Day of June, 2006

JON W. DUDAS
*Director of the United States Patent and Trademark Office*